(12) United States Patent
Fischell et al.

(10) Patent No.: US 9,550,067 B1
(45) Date of Patent: Jan. 24, 2017

(54) SHOE-SHAPED MAGNETIC COIL SYSTEM FOR THE TREATMENT OF FOOT PAIN

(71) Applicant: ZYGOOD LLC, Dayton, MD (US)

(72) Inventors: Susan R. Fischell, Dayton, MD (US); Robert E. Fischell, Dayton, MD (US)

(73) Assignee: Zygood, LLC, Dayton, MD (US)

( * ) Notice: Subject to any disclaimer, the term of this patent is extended or adjusted under 35 U.S.C. 154(b) by 0 days.

(21) Appl. No.: 14/921,452

(22) Filed: Oct. 23, 2015

(51) Int. Cl.
*A61N 2/02* (2006.01)
*A61N 2/00* (2006.01)

(52) U.S. Cl.
CPC ............... *A61N 2/008* (2013.01); *A61N 2/02* (2013.01)

(58) Field of Classification Search
None
See application file for complete search history.

(56) References Cited

U.S. PATENT DOCUMENTS

| 6,402,678 B1 | 6/2002 | Fischell et al. |
| 6,701,185 B2 | 3/2004 | Burnett et al. |
| 2002/0151760 A1* | 10/2002 | Paturu ............. A61F 5/41 600/15 |
| 2003/0158585 A1 | 8/2003 | Burnett |
| 2004/0210254 A1 | 10/2004 | Burnett et al. |
| 2011/0021863 A1* | 1/2011 | Burnett ............. A61N 2/008 600/14 |
| 2012/0302821 A1 | 11/2012 | Burnett |

FOREIGN PATENT DOCUMENTS

WO 9115263 A1 10/1991

\* cited by examiner

*Primary Examiner* — Charles A Marmor, II
*Assistant Examiner* — Thaddeus Cox
(74) *Attorney, Agent, or Firm* — Rosenberg, Klein & Lee

(57) ABSTRACT

A shoe-shaped magnetic coil system for the treatment of foot pain which has an electrical pulse generator and a magnetic coil system connected to the electrical pulse generator. The magnetic coil system is in the general shape of a shoe with the electric current pulses flowing through magnetic coils of the magnetic coil system being capable of creation of intense magnetic pulses within a patient's foot and ankle. The coil of wire is formed of coil sections having a smallest area in the region of the patient's toes with a generally increasing area of the coil sections as the ankle region is approached.

17 Claims, 2 Drawing Sheets

SHOE-SHAPED MAGNETIC COIL SYSTEM FOR THE TREATMENT OF FOOT PAIN

FIELD OF USE

This invention is in the field of methods and devices to be used by human subjects to decrease or eliminate foot pain without the use of ingested or injected drugs.

BACKGROUND OF THE INVENTION

It is well known that there are literally millions of patients throughout the world who suffer pain in various parts of their bodies. Three of the most frequent sites for pain are: (1) foot pain caused by chemotherapy or diabetic neuropathy; (2) shoulder pain often resulting from a tear or inflammation of the rotator cuff; and (3) lower back pain caused by a large variety of medical problems, particularly associated with the spine and the nerves surrounding the vertebrae. Although there are many pain medications to reduce the level of pain experienced by such patients, these drugs often are not sufficiently palliative and they typically can cause serious side effects.

One early invention to utilize magnetic fields to treat pain is described by Robert R, Holcomb in International Publication Number: WO 91/15263. The invention described in that document consists of four magnetic coils that are placed in the back of a chair or under a table where the patient's back would be exposed to the magnetic field. A DC current is placed through the four coils which results in an unchanging magnetic field to be experienced by the patient.

In U.S. Pat. No. 6,402,678, Robert E. Fischell, et al describe a device to be placed on the head which can eliminate or reduce the pain of migraine headaches by the application of a series of intense magnetic pulses. This device was approved by the US FDA on May 22, 2014 and is currently in use to treat patients with migraine headaches. The Fischell, et al migraine treatment device operates by charging capacitors to a high voltage and then discharging them into a magnetic coil to create a magnetic pulse as high as 0.8 Tesla in intensity. By Faraday's law, this changing magnetic pulse creates an electrical pulse within the skull that has been shown to eliminate migraine headaches. Because it takes about 45 seconds to charge the condensers from a battery within this Transcranial Magnetic Stimulation (TMS) device, the rate of applying magnetic pulses to the brain is extremely slow; i.e., typically about one pulse in about one minute. Even at that, the time rate of change of the magnetic field within the brain results in an electrical current in some neurons which eliminates most migraine headaches. However, the application of more pulses per unit time and at a higher magnetic field intensity with specially shaped magnetic coils could result in a more effective treatment for the relief of pain from other parts of the human body such as the feet for patients who suffer from diabetic neuropathy or cancer chemotherapy.

An existing system that is currently available to treat lower back pain is called TENS which is an acronym for Transcutaneous Electrical Nerve Stimulator. This device has two adhesive covered electrodes that are pasted onto the skin along the lower back. The device can then be turned on and adjusted so that the pain in the skin is acceptable while some electrical pulses enter the body in the vicinity of the spine where they can provide some relief for lower back pain. However, it would be highly advantageous to use a system that could provide higher intensity electrical pulses much deeper into the body without causing any skin pain. That can be accomplished with TransCutaneous Magnetic Stimulation or TCMS as described herein.

There is one issued patent and three patent applications by Donald Burnett et al namely U.S. Pat. No. 6,701,185 (the '185 patent), and the patent publications US2003/0158585 (the '585 publication), US2004/0210254 (the '254 publication) and US2012/0302821 (the '821 publication). The inventions described in the Burnett et al patent and publications all have a consistent design for the use of magnetic pulsations for the treatment of pain, namely, comparatively small wire coils with all wires being in circular form and placed against the skin of the foot or wrapped around the knee or elbow with the use of comparatively low electrical currents. Specifically, this prior art has the following numbers of generally circular or curved magnetic coils: the '185 reference 6 coils; the '585 reference, 10 coils; the '254 reference, 9 coils; and the '821 reference, 30 coils. Not even one of these 49 coil designs has even one straight wire section for placement anywhere on a human body. The Burnett et al references describe 23 different coil designs placed against the side of the foot and three different designs that are needles placed against the side of the foot. At no point in any of these prior art documents is there any design surrounding the foot and no Burnett et al design even closely approximates a shoe-shaped coil that is placed around the foot which is undoubtedly the optimum configuration for the application of magnetic pulsations to treat foot pain.

SUMMARY OF THE INVENTION

The present invention is a means and method to apply TransCutaneous Magnetic Stimulation (TCMS) to relieve pain in the foot of a human subject without the use of an analgesic drug. The TCMS system consists of an electrical pulse generator that would typically be plugged into a wall electrical socket and would provide by means of an attached magnetic coil repeated magnetic pulses into the entire foot and typically up into the patient's ankle. This type of coil could be extended further around the ankle to reduce pain in both the foot and the upper ankle. This unique design for a magnetic coil in the general shape of a shoe would be particularly advantageous for those patients who suffer foot and ankle pain resulting from extensive cancer chemotherapy or from diabetic neuropathy or the pain experienced at the bottom region of the foot which is called plantalgia that is caused by tissue inflammation at the bottom of the foot, which inflammation is called plantar fasciitis The optimum design for the coil for treating foot and ankle pain is to have the coil in the general shape of a shoe. This shape provides the greatest magnetic field onto the foot and ankle while using a minimum length of the wire and a minimum coil diameter so as to obtain the highest peak magnetic pulsations while minimizing the electrical voltage, electrical current and electrical power that is needed to treat the pain in that region. Furthermore, by having straight wires under the foot where that foot is generally flat and also having an increasing area of each single turn of wire in the coil as one proceeds from the toe toward the ankle, this novel design provides the highest possible magnetic field strength with the least electrical current and power and also the least coil heating during the pain treatment session. Still further, by having a thick, padded foam rubber or equivalent lining within the foot and ankle coil, fewer different size coils are needed to treat the variety of sizes of human feet that would be using this coil system for the treatment of foot and ankle pain. Still further, this soft inner lining for the foot and ankle coil system would provide a greater degree of comfort for the patients while using this device to reduce foot and ankle pain. Still further, an adjustable tilt platform could be used to adjust the angle of the shoe-shaped coil relative to the floor to optimize the comfort of the patient as he/she is sitting in a chair for an extended period of time to be treated for foot pain.

It should be understood that the electrical pulse generator would typically get its power by being plugged into a wall electrical socket. However, the use of a primary or rechargeable battery for the electrical pulse generator is certainly possible.

The waveform for treatment would be a magnetic pulse with a rise time between 10 and 500 microseconds. A pulse length of approximately 160±25 microseconds would be ideal for this purpose. The stimulation pulse rate would optimally be at a rate between 0.05 Hz and 10 Hz with an optimum pulse period being a pulse every 2 seconds to a pulse every 10 seconds which is essentially 0.1 Hz to 0.5 Hz. It is also conceived that the wave form could be approximately half of one sine wave or a square wave to optimize the relief of pain. The peak amplitude for the magnetic pulses at the patient's skin should be at least 0.3 Tesla with an optimum magnetic pulse strength at the skin being between 0.8 and 3.0 Tesla. To accomplish this level of peak magnetic pulse intensity, it would be typical to have a peak electrical current in the coil that could be as small as 500 Amperes or as strong as 10,000 Amperes. The peak pulse voltage to accomplish these intense levels of electrical current could be between 500 and 10,000 Volts.

Thus one object of the present invention is to provide a means and method to treat foot and/or foot and ankle pain of a human patient by the application of high intensity magnetic pulsations through the patient's skin at that location where those magnetic pulsations create subcutaneous electrical current pulses that reduce the level of pain in the foot or in both the foot and the ankle.

Another object of this invention is to optimize the size and shape of the magnetic coil to best fit that patient's foot and/or foot and ankle thereby minimizing the electrical power, current and voltage required to obtain the required high levels of magnetic pulsations to be experienced by the patient's foot or the entire foot and the ankle.

Still another object of this invention is a method to diminish the pain caused by diabetic neuropathy in the foot and/or foot and ankle.

Still another object of this invention is a method to diminish the pain caused by cancer chemotherapy in the foot and/or foot and ankle.

Still another object of this invention is a method to diminish the pain within the tissue at the bottom of the foot, which pain is called plantalgia.

Still another object of this invention is to have the magnetic coil in the general shape of a shoe which provides the maximum magnetic field onto the entire volume of the patient's foot and ankle with the least electrical current, voltage and power.

Still another object of this invention is to have straight wire sections at the bottom of the shoe-shaped coil for optimum creation of the magnetic field within the patient's foot and for optimum comfort for the patient during the extended time period required for the treatment of foot pain.

Still another object of this invention is to have a thick padding within the coil that surrounds the foot so that patients with at least three different shoe sizes could use the same coil system.

These and other objects and advantages of this invention will become obvious to a person of ordinary skill in this art upon reading the detailed description of this invention including the associated drawings as presented herein.

DETAILED DESCRIPTION OF THE INVENTION

Figure 1:
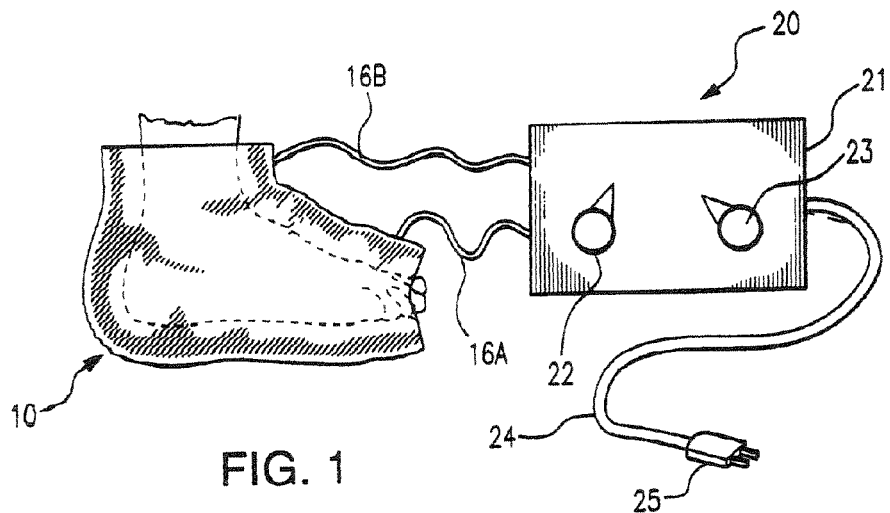
FIG. 1 illustrates a magnetic coil placed around the foot and ankle of a patient for the treatment of foot and/or foot and ankle pain, the coil being connected to an electrical pulse generator that is plugged into a wall socket.

FIG. 1 illustrates a TransCutaneous Magnetic Stimulator (TCMS) magnetic coil system 10 connected to an electrical pulse generator system 20 for the treatment of foot and/or foot and ankle pain. The electrical pulse generator system 20 receives its electrical power through the wire 24 that is connected to the plug 25 that would be placed into a conventional electrical socket (not shown). The electrical pulse generator system 20 would be capable of providing the pulses of electrical current that go through the foot coil 10 for the creation of intense magnetic pulsations within the coil 10 for the treatment of foot and ankle pain.

Figure 2:
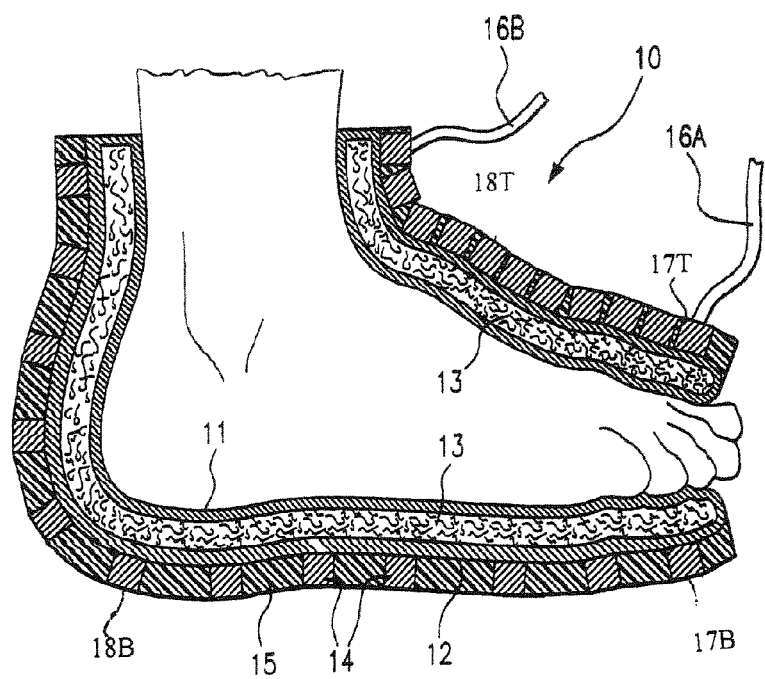
FIG. 2 is a cross section of a magnetic coil placed around the foot and ankle of a patient for the treatment of foot pain or for the treatment of foot and ankle pain.

Although the optimum electrical pulse generator system 20 would get its power as shown in FIG. 1, it is also conceived that the electrical pulse generator 21 could get its power from a primary or a rechargeable battery. The dials 22 and 23 on the face of the electrical pulse generator 21 would be used to adjust the pulse frequency and pulse amplitude for the electrical current pulses created by the electrical pulse generator system 20 to create the magnetic pulses that would be delivered by the magnetic coil system 10. These electrical current pulses would be delivered to the magnetic coil system 10 by means of the wires 16A and 16B as shown in FIGS. 1 and 2. Electrical pulses with a pulse amplitude as high as 10,000 Amperes could be generated by the pulse generator 21. The lowest pulse amplitude would be at least 500 Amperes to obtain the desired intensity for the magnetic pulses to be delivered by the magnetic coil system 10. The optimum electrical current being between 800 and 1,200 Amperes. It should also be understood that the pulse generator system could also have separate controls to control other pulse variables such as the pulse duration, the pulse amplitude, the number of pulses to be used for a treatment and the time between each pulse. Of great importance is to utilize a wire size that will not create undue heating of the coil 10 during a treatment for pain. To that end, it is optimum to utilize copper or aluminum wire sizes that lie between #2 AWG and #6 AWG. These wire sizes are required to keep the heating effect from the electrical pulses through the coil from reaching too high a temperature for a typical 10 to 30 minute treatment time period for each patient. This is in contradistinction to the Burnett et al '185 patent that preferably utilizes #12 AWG coil wire size which would result in the creation of excessive coil heating for the levels of magnetic field intensity that are required for obtaining significant pain relief. The Burnett et al '185 patent also describes the use of wire sizes from as low as #10 AWG to as high as #20 AWG, none of which would be suitable for the maintenance of a reasonable coil temperature when using the high levels of electrical current as required for effective treatment of foot pain.

The electrical pulse generator system 20 would include conventional circuitry to generate a pulse waveform, a sinusoidal wave form, a square wave waveform or any other pulse wave form that is found to be effective for stimulation of nerves. The frequency of the pulses could be anything between 0.1 Hz and 10 Hz with an optimum pulse rate being approximately 0.5 to 1.0 Hz. The pulse amplitude generated by the magnetic coil 10 could be anything between 0.3 Tesla and 5.0 Tesla with an optimum magnetic pulse peak intensity being between approximately 0.5 and 3.0 Tesla. None of the Burnett et al publications or his single patent describes the level of magnetic field strength that is required to provide foot and ankle pain relief for a human subject. When pulses are used for TCMS, the pulse rise time could be between 10 and 500 microseconds with an optimum pulse rise time being approximately 160±25 microseconds. The Burnett et al '185 patent suggests the use of pulse durations as high as 200,000 microseconds (i.e., 200 milliseconds) which would be completely unacceptable to generate the high rate of change of the magnetic pulses that is required to obtain sufficiently high electrical currents within the foot and ankle to generate by Faraday's Law an adequate electrical current pulse for the electrically conducting human tissue within the foot and ankle to eliminate pain.

FIG. 2 is a cross section of the magnetic coil system 10 placed around the foot and ankle of a patient who suffers from foot pain or foot and ankle pain. This pain would typically be caused by extensive cancer chemotherapy or would be a result of diabetic neuropathy or from plantalgia. The inner lining 11 of the magnetic coil system 10 would be situated closely around the patient's foot and ankle. Surrounding the inner lining 11 would be a soft elastic material 13 that is contained within the inner lining 11 and the outer covering 12. It should be noted that (as shown in FIG. 2) the inner lining 11 and outer covering 12 could in fact be formed from one piece of material such as leather or a plastic material such as Nylon. The soft elastic material 13 may be porous and could be formed from a material such as cotton or foam rubber or any other material that would make it moderately easy for the patient to place his/her foot within the magnetic coil system 10. It is also conceived to have the patient wear a tight fitting and somewhat slippery sock when placing his/her foot into the magnetic coil system 10. That would be especially needed if the same magnetic coil system 10 is made available in a commercial medical facility for many different patients.

A great advantage of the design shown in FIG. 2 is that patients with as many as three different shoe sizes could fit into the coil system 10 shown in FIG. 2. For example, if the maximum foot size that could fit into the coil system 10 of FIG. 2 was a ten, then this design could also accommodate sizes eight and nine without losing any significant strength of the magnetic field experienced by the patient who would use that shoe-shaped coil system. It is also expected that the shoe sizes that could be used with the coil system 10 could go from as small as a woman's size four to as large as a man's size fifteen. In none of the Burnett et al publications or patent is there any mention of a coil in the form of a shoe into which a patient suffering from foot and ankle pain could place his/her foot. Only this shoe-shaped coil has the appropriate shape for treating foot pain.

FIG. 2 also shows the cross section of square wire magnetic coil 14 that is wrapped around the outer covering 12. A total of 12 turns of the magnetic coil 14 are shown in FIG. 2. Any number of turns between 4 and 30 could be used for such a magnetic coil 14 with an optimum number of turns being approximately 14±7 turns. It should also be understood that the wire of the coil 14 would be insulated on its exterior and would have a cross section that could be of any one of several different shapes as shown in FIG. 3.

Surrounding the magnetic coil 14 would be a thin coil covering member 15 that could be formed from a plastic material or from certain cloth materials. It should also be understood that the wires 14 could be adhesively attached to the outer layer 12 or there could be a plastic fill material 15 situated between each turn of the wires of the magnetic coil 14. FIG. 2 also shows the wires 16A and 16B which are attached to the electrical pulse generator 20 as shown in FIG. 1.

Of great importance to the design of an effective coil system 10 for the treatment of foot and ankle pain, is the shape of that coil 10 which is generally in the novel shape of a shoe. Specifically, the bottom coil wires 17B and 18B at the bottom of the shoe-shaped coil 10 are essentially straight wires situated transverse to the length of the foot and they are as close as reasonably possible to the bottom of a human foot. This unique design for the coil 10 provides the maximum magnetic field intensity onto the bottom tissue of the foot that especially optimizes the treatment of pain for a condition such as plantalgia. The top portions of the coil 10, namely the top curved coil wires 17T and 18T have a curved shape to conform to the generally curved top surface of a human foot. If we look at the cross-sectional area of the foot coil 10 having a bottom portion of the wire 17B with a top portion of the coil turn wire 17T we see that the area of that turn of the coil wires 14 is decidedly less than the area of the turn of the coil with a bottom wire 18B and a top portion wire 18T. This increasing cross-sectional area is another unique feature of the design of the coil 10 which is that the area of each successive coil around the foot increases in area as one moves from the toe to the ankle. None of the Burnett et al references has any coil with series of straight wires connected to a series of curved wires nor does any Burnett et al have a coil with an increasing inside area as one moves from the toe toward the ankle of a shoe-shaped coil design.

Figure 3:
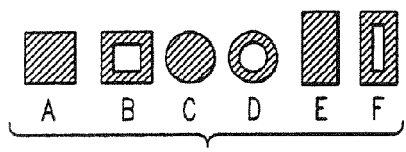
FIG. 3 illustrates cross sections of various wires that could be used for the magnetic coil.

As seen in FIG. 3, the cross section of the wire could be square (FIG. 3A) square but hollow (FIG. 3B) round (FIG. 3C) round with a hollow interior (FIG. 3D) rectangular (FIG. 3E) and rectangular with a hollow interior (FIG. 3F). Either gas or a liquid such as water could be made to flow through any one of the hollow wires in order to either heat or cool the wire to provide additional comfort for a patient that is using the shoe-shaped coil to relieve foot and ankle pain.

Figure 4:
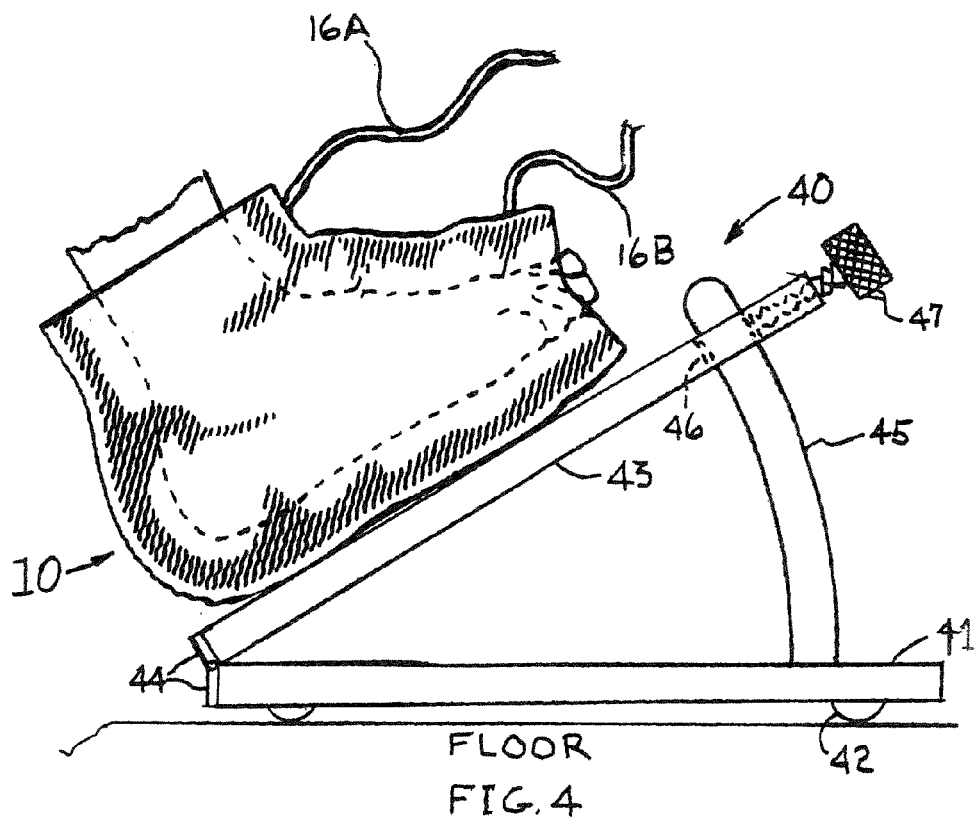
FIG. 4 is a side view of an adjustable angle foot platform.
Figure 5:
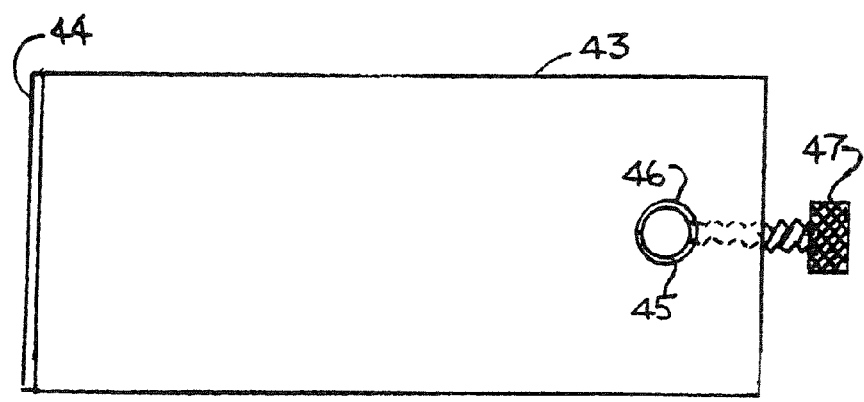
FIG. 5 is a top view of the adjustable angle foot platform of FIG. 4.

FIG. 4 is a side view and FIG. 5 is a top view of an adjustable tilt table 40 onto which the shoe-shaped coil 10 can be placed by the patient. The tilt table 40 has a bottom platform 41 with four rubber or plastic buttons 42 underneath for preventing the tilt table 40 from sliding on the floor. The top platform 43 has a hinge 44 that attaches it to the bottom platform 41. The top platform 43 also has a hole 46 through which can slide a round, curved metal cylinder 45 which is used to adjust the angle "a" of the top platform 43 relative to the bottom platform 41. The knurled handled screw 47 can be loosened to adjust the angle "a" of the top platform 43 and can then be tightened to hold that angle fixed relative to the bottom platform 41. By this means, the coil system 10 that is connected by the wires 16A and 16B to the pulse generator (not shown) can be adjusted for the optimum comfort of the patient as he/she undergoes a somewhat lengthy procedure for the treatment of foot and ankle pain.

Various other modifications, adaptations and alternative designs are of course possible in light of the teachings as presented herein. Therefore it should be understood that, while still remaining within the scope and meaning of the appended claims, this invention could be practiced in a manner other than that which is specifically described herein.

What is claimed is:

1. A system for eliminating or reducing foot pain or both foot and ankle pain of a patient, the system comprising:
    an electrical pulse generator for producing a series of electrical current pulses and having a peak current pulse amplitude of between 500 to 10,000 Amperes; and
    a magnetic coil system formed in the general shape of a sneaker which is open in a region of a patient's toes with the coil system being electrically connected to the electrical pulse generator, the magnetic coil system adapted for insertion therein of a patient's foot and ankle, the electrical current pulses flowing through the magnetic coil formed of an electrically conducting coil of wire surrounding said patient's foot and ankle being capable of creating magnetic pulses having a peak amplitude of at least 0.3 Tesla within the patient's foot and ankle that, in turn, create electrical currents within the patient's foot and ankle, these electrical currents having a capability of decreasing pain experienced by the patient in a foot and an ankle of said patient, said electrically conducting coil of wire formed of coil sections, each of said coil sections defining an interior cross-sectional area wherein said interior cross-sectional area of said coil sections increases between an area adjacent to said patient's toes to an area adjacent said ankle of said patient, and the coil sections situated beneath the patient's foot being substantially straight wires situated in a transverse direction underneath the patient's foot to generally conform to generally straight surfaces that exist underneath the patient's foot in a direction which generally extends in a direction perpendicular to a longitudinal direction which is along the length of the patient's foot.

2. The system of claim 1 wherein the electrical pulse generator includes controls to adjust a frequency and amplitude of the electrical current pulses produced by the electrical pulse generator.

3. The system of claim 1 wherein the magnetic coil system is adapted to extend beyond the patient's foot and onto the ankle of that patient.

4. The system of claim 1 wherein the electrical pulses created by the electrical pulse generator create magnetic pulses have a rise time to a point of maximum intensity of the created magnetic field that is between 10 and 500 microseconds.

5. The system of claim 4 wherein the magnetic pulses have a rise time to a point of maximum intensity of the magnetic field of approximately 160±25 microseconds.

6. The system of claim 4 wherein a maximum intensity of the magnetic pulses created by the magnetic coil system is between approximately 0.5 and 3.0 Tesla.

7. The system of claim 1 wherein a peak electric current pulse emanating from the electrical pulse generator is between approximately 800 and 1,200 Amperes.

8. The system of claim 1 wherein the electrically conducting coil has approximately 14±7 turns of an electrically conducting, insulated wire adapted to generally surround the patient's foot or both the patient's foot and ankle.

9. The system of claim 1 wherein the magnetic coil system includes a lining material adapted for placement of the patient's foot for treatment with said magnetic pulses.

10. The system of claim 1 wherein said magnetic coil system includes a sponge-like material adapted to be placed between the electrical conducting coil of wire and the patient's foot so that patients with as many as three different shoe sizes could fit into that specific magnetic coil.

11. The system of claim 1 wherein wires for the magnetic coil have a cross section selected from the group that includes the following cross-sectional geometries: square, hollow square, round, hollow round, rectangular and hollow rectangular.

12. The system of claim 11 wherein the wires for said magnetic coil that have cross-sections a either a hollow square or hollow round or hollow rectangular have a heating or cooling liquid or gas flowing within the hollow square wire, the hollow round wire, or the hollow rectangular wire to improve a comfort level of the patient who is being treated with magnetic pulses.

13. A method to reduce foot and ankle pain of a patient that suffers from diabetic neuropathy or from extended use of chemotherapy or from plantalgia, the method including the following steps:
    a) establishing an electrical pulse generator system for producing electrical current pulses having a peak magnitude that is between 500 and 10,000 Amperes;
    b) connecting the electrical pulse generator system to a magnetic coil system that is formed in a general shape of a sneaker which is open in a region of a patient's toes,
    c) placing the patient's foot into the magnetic coil system formed of coil sections, each of said coil sections defining an interior cross-sectional area wherein said interior cross-sectional area of said coil sections increases between an area adjacent to said patient's toes to an area adjacent said ankle of said patient, and said coil sections configured to underlay said patient's foot in a transverse direction relative to a longitudinal length of the foot, and being substantially formed of straight wires underlying said patient's foot from one side to an opposing side of the patient's foot; and
    d) turning on the electrical pulse generator so as to create magnetic pulses having a peak magnetic field intensity of at least 0.3 Tesla, the magnetic pulses being created within the magnetic coil system so as to diminish or eliminate the pain felt by said patient in that patient's foot and ankle.

14. The method of claim 13 wherein the step of applying magnetic pulses includes applying an amplitude of the magnetic pulses delivered by the magnetic coil system having a peak amplitude in a range between 0.5 to 3.0 Tesla.

15. The method of claim 13 wherein the step of applying magnetic pulses includes the step of selectively adjusting an amplitude of the magnetic pulses delivered onto the patient's foot to have a peak magnitude of at least 0.5 Tesla.

16. The method of claim 13 including the patient placing a second foot into the magnetic coil system after a first foot to be treated has completed a treatment for that first foot of that patient.

17. A magnetically actuated boot comprising:
    a boot housing adapted for insertion of a patient's foot and extending in a longitudinal direction;

an electrical pulse generator for producing a series of electrical current pulses having a peak amplitude of between 500-10,000 Amperes, a magnetic coil system located within said boot housing, said magnetic coil system electrically connected to said electrical pulse generator, said magnetic coil system composed of an electrically conducting coil of wire formed of coil sections wherein said coil sections have a decreased cross-sectional internal area in the vicinity of said patient's toes and an increased cross-sectional internal area as said coil sections approach said patient's ankle; and, each of said coil sections having a plurality of wire sections located beneath said patient's foot with each of said wire sections extending from one side of the patient's foot opposing side of the patient's foot.

\* \* \* \* \*